United States Patent [19]

Holtkamp

[11] Plant 5,025

[45] Apr. 5, 1983

[54] AFRICAN VIOLET PLANT

[76] Inventor: Reinhold Holtkamp, Werther Strasse 112, 4294 Isselburg, Fed. Rep. of Germany

[21] Appl. No.: 300,676

[22] Filed: Sep. 9, 1981

[51] Int. Cl.[3] ..... A01H 5/00
[52] U.S. Cl. ..... Plt./69
[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new cultivar of African violet known by the cultivar name Margit having numerous relatively small leaves and a profuse flowering corolla. Violet blossoms are carried on very upright and strong flower stems, the center of each blossom being relatively darker, velvety and shiny. The variety has a uniform growth habit, and provides an attractive saleable plant within 7–9 weeks after potting, with flowering being essentially continuous.

1 Drawing Figure

The present invention comprises a new and distinct cultivar of African violet plant, botanically known as *Saintpaulia ionantha,* and hereinafter referred to by the cultivar name Margit.

The new cultivar was referred to during the breeding and selection process by the designation d 198/2, and is a product of a planned breeding program. The basic objective of the breeding program was to create a new African violet cultivar having a compact growth habit with upright and compact flower head, and deep violet flower color.

The new cultivar was originated from a cross made in a controlled breeding program in Isselburg, West Germany. The female, or seed parent was a cultivar designated 26 BI blue. The male, or pollen parent was a cultivar designated b 36/1 blue frilled.

The new cultivar Margit was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Margit has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Margit, which in combination distinguish this African violet as a new and distinct cultivar:

1. Compact growth habit with relatively small leaves.
2. Very upright and strong flower stems, forming a compact and profuse corolla.
3. Nine or more flower stems, with 6–9 or more flowers per stem.
4. Center of flower is dark, velvety and shiny.
5. Uniform in growth.

6. Attractive saleable plant with compact corolla within 7–9 weeks after potting.
7. Flowers almost continuously.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Margit.

Parentage:

*Male parent.*—b 36/1 blue frilled.

*Female parent.*—26 BI blue.

Propagation: The new cultivar holds its distinguishing characteristics through successive propagations by leaf cuttings and by division of shoots.

Plant: From 7 cm. to 9 cm. tall when grown in pots, and approximately 22 cm. in diameter when fully grown.

Leaves:

*General form.*—Heart-shaped, small.

*Diameter.*—45–55 mm.

*Texture.*—Leathered, slightly hairy.

*Aspect.*—Shiny.

*Veins.*—Upperside slightly visible; underside well-pronounced, light green and hairy.

*Color (upperside).*—HCC parsley green 00962.

*Color (underside).*—HCC willow green 000862/1.

*Petiole.*—Young petiole hairy, brownish, underside with green tinge; old petiole slightly lighter.

Flowers:

*Buds.*—Ball-shaped; 6 mm. just before opening; 6–9 or more per stem.

*Sepals.*—Color: Brownish green. Calyx: Flat, funneled. Aspect: Spear-shaped, hairy. Peduncle: Strong, upright above leaves, tilted towards center; brownish green, hairy.

Individual flowers:

*Size.*—35–40 mm.

*Color.*—(Upperside): Victoria violet 738, center a tone deeper. (Underside): Victoria violet 736/3.

*Borne.*—Flower stem carries 6–9 or more flowers on strong upright peduncles; flowers occasionally display an additional small petal in center of bloom and even up to 7 petals.

*Shape.*—Conventional (2 small and 3 larger petals).

*Flowering time.*—First flowers appear 7–8 weeks after potting; after 10 weeks full flowering saleable plant.

Reproductive organs:

*Stamens.*—2 anthers, composed of 2 cells, with seed capsule pushed slightly through.

*Anthers.*—HCC Dresden yellow 64.

*Filaments.*—3 mm. long; yellowish green with partly purple.

*Styles.*—7 mm., campanola violet 37; base of ovary light green, slightly hairy.

*Pollen color.*—HCC Dresden yellow 64/3.

Roots: White when young and active; greenish brown when older; normally developed.

Disease resistance: Good as experienced to date.

General observations: Margit is a normal and compact growing variety with many small leaves and a profuse flowering corolla. Its upright strong flower stems carry up to nine or more single blossoms. It flowers almost continuously. The flowers do not fade, and are very long-lasting and non-dropping.

I claim:

1. A new and distinct cultivar of African violet known by the cultivar name Margit, and particularly characterized by the combined features of compact growth with relatively small leaves, very upright and strong flower stems which form a compact and profuse corolla; nine or more flower stems, with 6–9 or more violet flowers per stem, center of flower is relatively darker, velvety and shiny; uniform growth habit; almost continuous flowering, and by its ability to provide an attractive saleable plant with a compact corolla within 7–9 weeks after potting.

* * * * *

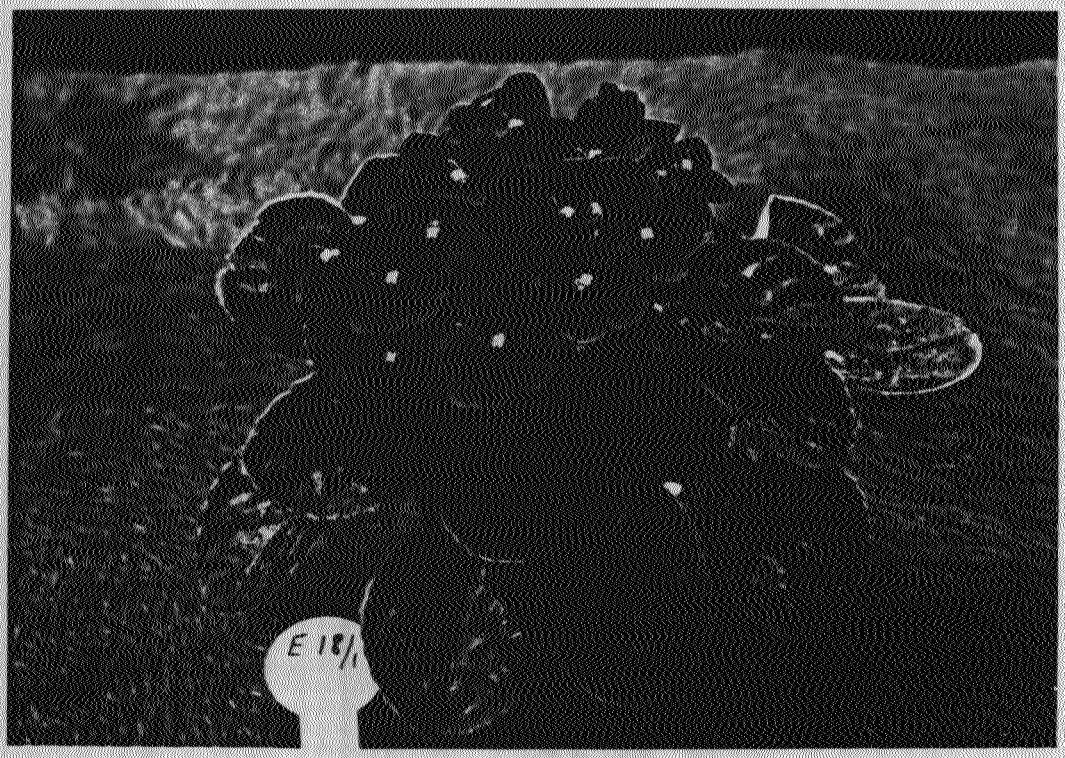
E 18/1

UNITED STATES PATENT AND TRADEMARK OFFICE

CERTIFICATE OF CORRECTION

PATENT NO. : Plant 5,025

DATED : April 5, 1983

INVENTOR(S) : Reinhold Holtkamp

It is certified that error appears in the above-identified patent and that said Letters Patent is hereby corrected as shown below:

On the heading of the colored photographic drawing "Plant 5,025" should read -- Plant 5,020 --, and "Plant 5,020" should read -- Plant 5,025 --.

Signed and Sealed this

*Fifteenth* Day of *April 1986*

[SEAL]

*Attest:*

*Attesting Officer*

DONALD J. QUIGG

*Commissioner of Patents and Trademarks*